United States Patent [19]

Masetti et al.

[11] Patent Number: 5,268,746
[45] Date of Patent: Dec. 7, 1993

[54] DEVICES FOR MEASURING THE OPTICAL ABSORPTION IN THIN LAYER MATERIALS BY USING THE PHOTOTHERMAL DEFLECTION SPECTROSCOPY

[75] Inventors: Enrico Masetti; Marco Montecchi, both of Rome, Italy

[73] Assignee: Ente per le Nuove Tecnologie, l'Energia e l'Ambiente (ENEA), Rome, Italy

[21] Appl. No.: 921,968

[22] Filed: Aug. 4, 1992

Related U.S. Application Data

[63] Continuation of Ser. No. 581,635, Sep. 12, 1990, abandoned.

Foreign Application Priority Data

Sep. 26, 1989 [IT] Italy ............................. 48405 A 89

[51] Int. Cl.⁵ .......................................... G01N 21/00
[52] U.S. Cl. ...................................... 356/432; 356/128
[58] Field of Search ................. 356/432, 432 T, 128, 356/129, 130

[56] References Cited

U.S. PATENT DOCUMENTS

| | | | |
|---|---|---|---|
| 4,562,350 | 12/1985 | Tirouard et al. | 250/239 |
| 4,589,783 | 5/1986 | Thomas et al. | 356/432 T |
| 4,813,763 | 3/1989 | Saito et al. | 350/169 |
| 4,830,502 | 5/1989 | Saito et al. | 356/432 |

FOREIGN PATENT DOCUMENTS

| | | |
|---|---|---|
| 0094274 | 4/1983 | France . |
| 2174491A | 4/1985 | United Kingdom . |
| 2162942A | 8/1985 | United Kingdom . |

*Primary Examiner*—Richard A. Rosenberger
*Attorney, Agent, or Firm*—Stevens, Davis, Miller & Mosher

[57] ABSTRACT

A device measuring the optical absorption in thin layer materials by using the photothermal deflection spectroscopy (P.D.S.) comprises a laser source, an optical doubler between the laser source and the probe intended to divide the laser beam in two equal, parallel measurement and control beams, a cylindrical lens between the doubler and the probe, and a pair of position sensors which receive the beams focused by said lens and send them to an electronic circuit supplying a signal output which is not influenced by the noise due to the instability in the direction of the analyzer beam and to the mechanical vibrations.

16 Claims, 3 Drawing Sheets

DEVICES FOR MEASURING THE OPTICAL ABSORPTION IN THIN LAYER MATERIALS BY USING THE PHOTOTHERMAL DEFLECTION SPECTROSCOPY

This application is a file-wrapper continuation of application Ser. No. 581,635, filed Sept. 12, 1990 now abandoned.

The present invention relates to an improved device for measuring the optical absorption in thin layer materials by using the photothermal deflection spectroscopy. More particularly this invention relates to an opto-electronic device for reducing the effects associated to the instability in the direction of the analyzing beam due to inherent phenomena of the laser and to the mechanical vibrations in a measuring instrument called "Photothermal Deflection Spectroscopy" (P.D.S.).

The measurement of the optical absorption of thin covering for optical systems has become more and more important in the last years due to the increasing spread of the optical devices and in particular of the laser sources in the industrial processes.

A measuring system which has been successful, even though it is not free of drawbacks, is the above mentioned P.D.S. system which allows the energy absorbed by a sample and transformed into heat to be measured. Even though said system allows obtaining very important results, it comes up against a serious limitation in trying to deal with measurements on an industrial scale and not only in research laboratories because of the remarkable incidence of the noise on the reliability of the measurements.

Thus the measurement is strongly biased by the noise because of the high sensitivity of the sensor, and then it is necessary to use a phase lock analyzer operating at a preset modulation frequency in order to obtain the "real" signal, as it is better understood hereinafter. The noise has several sources:

a) instability of the sighting of the analyzing laser beam;

b) instability of the power of said laser beam;

c) turbulence of liquids and gases crossed by the analyzing beam;

d) mechanical vibrations of several components;

e) electronic circuit noise.

At present the following arrangements are provided to decrease the incidence of said noise. For example:

a) and b): using lasers of high quality;

c): intubating, where possible, the analyzing laser beam in hollow cylinders (better vacuum cylinders) or cylinders which can be filled with transparent materials such as plexiglas, glass or other suitable material;

d): providing anti-torsion mounting and antivibration optical benches;

e): using instruments of high quality.

Many of said arrangements, in particular those of item d), require a considerable financial burden and moreover remarkably increase weight and size of P.D.S. apparatus.

It should be noted that a good anti-vibration bench should have a complex pneumatic suspension system and a high inertial mass, i.e. a heavy weight. Obviously this is a limit to the spreading of the technique.

The object of the invention is to reduce the effects caused by the mechanical vibration d) and the instability of the analyzing laser beam a) at very low cost since only an optical system for splitting the analyzing laser beam, two position sensors and a suitable electronic circuit are required.

According to the invention there is provided an opto-electronic device which is part of an absorption measuring system using P.D.S. and allows both the noise generated by the mechanical vibrations and the noise due to the direction instability of the analyzing laser beams to be strongly reduced, and then the sensitivity of the apparatus to be increased.

A real advantage achieved by the present invention is that the P.D.S. apparatus does not need to be placed on anti-vibration tables, thus providing a wider spread in the industrial field. Another advantage is the very low cost.

The invention will be now described with reference to the annexed drawings showing by way of example a preferred, non-limitative embodiment of the invention.

Figure 1:
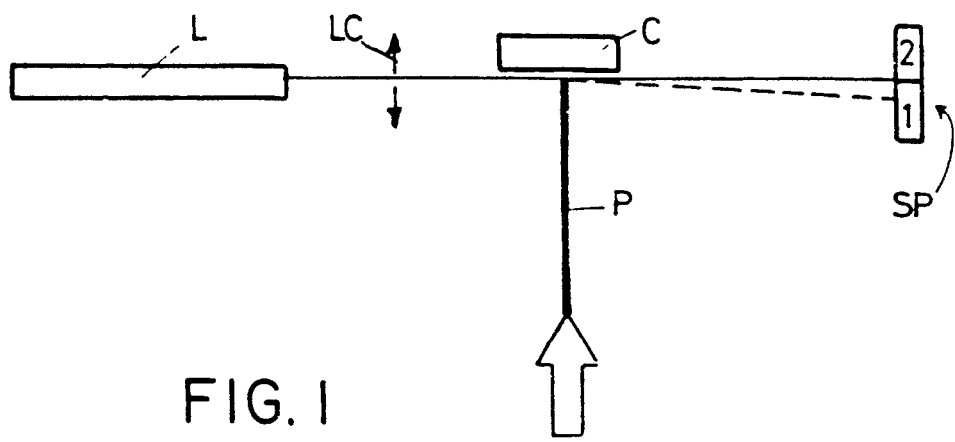
FIG. 1 shows schematically the operating principle of a transversal P.D.S. apparatus.
Figure 2:
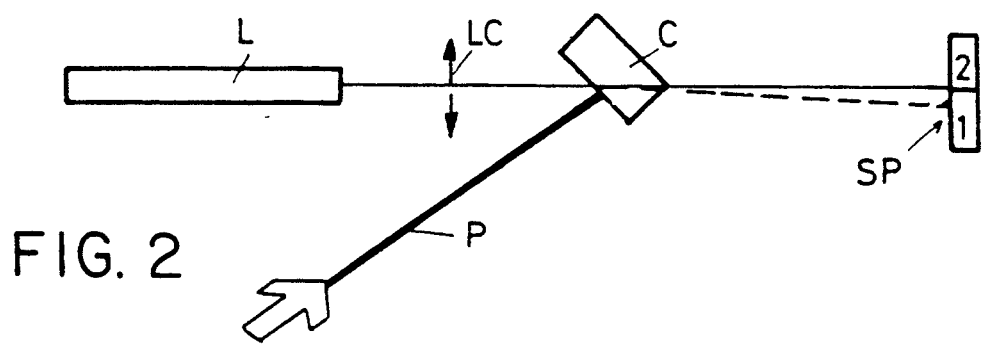
FIG. 2 shows the operating principle of a collinear P.D.S. apparatus.

The heat transmission from the sample to the environmental medium (generally a transparent fluid) causes in the latter a gradient of the refractive index able to deviate a laser beam crossing said medium. The amount of such a deviation is proportional to the absorbed electromagnetic radiation. The proportionality constant is provided by measuring under the same conditions the deviation relative to a sample having a known absorption. Absorptions up to $10^{-6}$ can be presently measured by P.D.S. techniques. In FIGS. 1 and 2 the diagrams of a "transversal" and a "collinear" P.D.S. apparatus for measuring samples under the form of thin layers are shown, respectively. A transversal P.D.S. (Photothermal Deflection Spectroscopy) apparatus is a P.D.S. apparatus wherein the measurement beam flies over the sample surface in the area stressed by the pump beam and the pump beam moves in a direction transverse to the direction of the laser.

Figure 3:
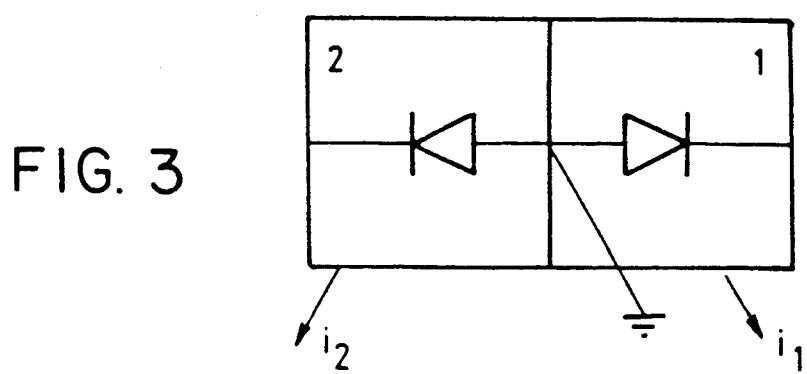
FIG. 3 shows the diagram of a two-sector position sensor.
Figure 4:
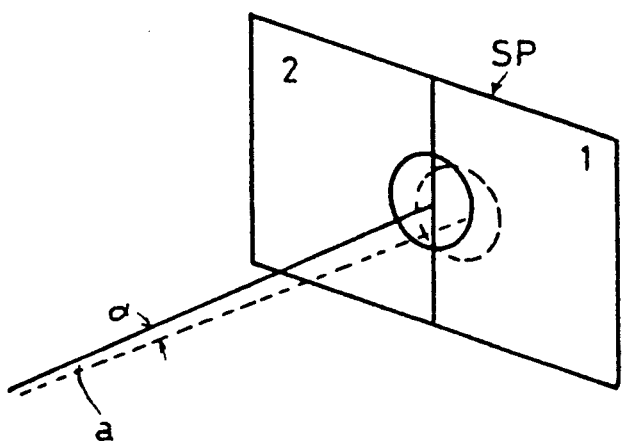
FIG. 4 shows the operation of the position sensor with a laser beam.

A collinear P.D.S. apparatus is a P.D.S. apparatus wherein the measurement beam crosses the sample in the area stressed by the pump beam and the pump beam moves in the same direction as the laser beam. The electromagnetic radiation of pump P from either a lamp followed by a monochromator or a laser beam hits sample C in the analyzed field. The analyzing beam from a laser L (tipically a He-Ne laser of a few milliwatts power) is focused by a converging lens LC so that near the sample the transversal dimension of the beam is lower than that of the beam of pump P. In the arrangement of FIG. 1 the focusing further allows the distance between the analyzing laser beam and the sample to be reduced with consequent increase of the sensitivity (the amplitude of the thermal wave generated by the heating of the sample is being reduced in the exponential form while moving away from the surface). To increase the deviation the medium in which the sample is immersed should have a high gradient of the refractive index as a function of temperature. Generally the position sensor SP is formed of a pair of adjacent, opposed photodiodes. In FIG. 3 a two-sector position sensor is shown; it is centrally placed with respect to the laser spot (without absorption) and is oriented so that the axis of the photodiodes is almost parallel to the plane in which the deviated beams from the analyzing beam due to the absorption are lying (FIG. 4).

Figure 5:
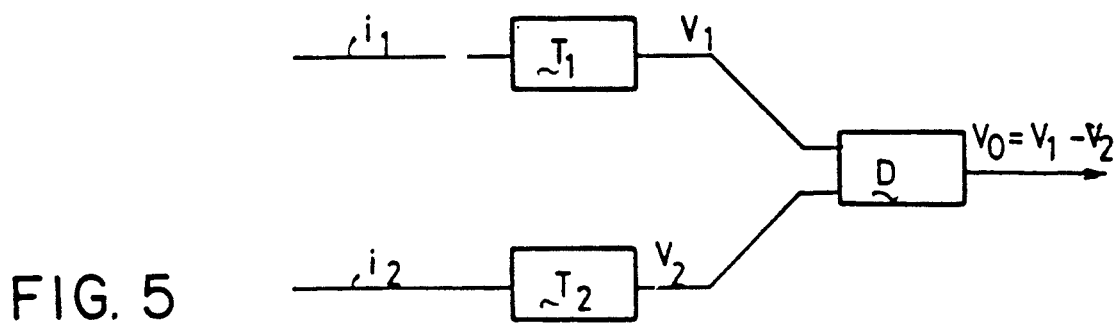
FIG. 5 shows the block diagram of the electronic circuit associated to the position sensor.

The two photocurrents are transformed into voltages by a suitable electric circuit (FIG. 5) supplying an output proportional to their difference. For small values of angle "a" of FIG. 4 the output signal of the circuit of FIG. 5 is modulated at the same frequency as that of modulation of the electromagnetic pump radiation, and the value thereof is proportional to the absorption of the sample.

Figure 6:
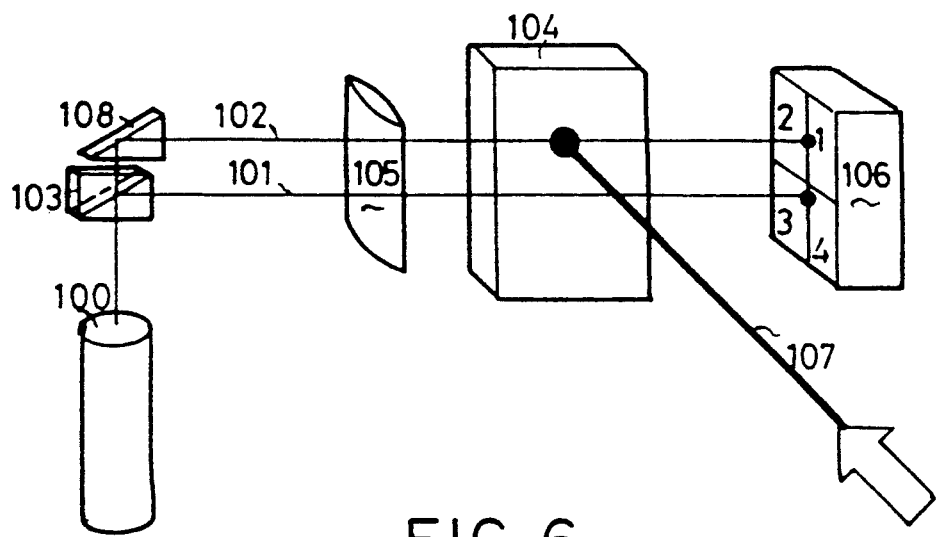
FIG. 6 shows the application of the invention to a transversal P.D.S. system (the application to a collinear P.D.S. system is similar)

In FIG. 6 the device according to the invention is schematically shown. The analyzing beam 100 generated by a laser source is split in a measurement beam 102 and a control beam 101 by means of an optical system consisting of an optical splitting head 103, which split the input beam into two beams of the same intensity having directions orthogonal to each other, and a prism providing a total internal reflexion and allowing, once it is suitably positioned, the measurement beam to be disposed parallel to the control beam at the desired mutual distance.

Both beams 101 and 102 are focused in a plane perpendicular to the surface of the sample 104 by a converging cylindrical lens 105 and they run in parallel to each other the distantc ebetwen the lends and the two sector position sensor 106 which in the illustrated embodiment has four quadrants. However, only measurement beam 102 passes through the area of the sample illuminated by the pump beam 107. The measurement beam and the control beam hit the sensor so as to evenly illuminate (without absorption) each a couple of sectors.

Let it be assumed that the couple 1, 2 is illuminated by the measurement beam and the couple 3, 4 by the control beam. The four photocurrents thus generated are conveyed to an electronic circuit the output of which is a linear combination thereof with alternate signs:

$$V = a1^* i1 + a2^* i2 + a3^* i3 + a4^* i4$$

where "a" is the deviation angle with respect to the central direction.

Figure 7:
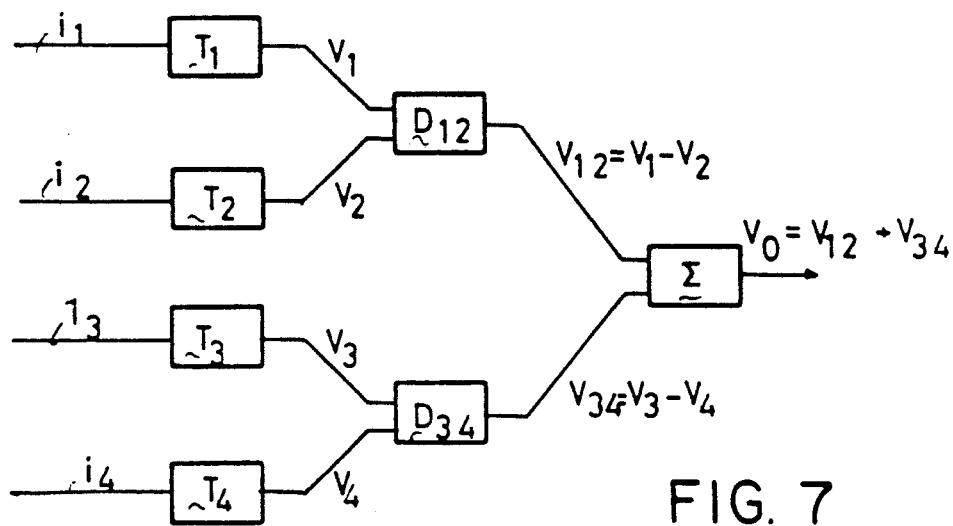
FIG. 7 shows the block diagram of the electronic circuit associated to the position sensor in the four-sector arrangement.

In FIG. 7 the block diagram of an embodiment of the above mentioned electronic circuit is shown. If am and ac are the deviations of the measurement beam and the control beam, respectively, and R is the spot radius of the analyzing beam and L is the distance between the sample and the sensor it will result in case of small deviations (am and ac $< R/L$):

$$V(am, ac) = Im^*D12/2^*(S1^*T1^*(1 + am/aOm) - S2^*T2^*(1 - am/aOm) + Ic^*D34/2^*(S3^*T3^*(1 - ac/aOc) - S4^*T4^*(1 + ac/aOc)$$
$$dV/dam = Im^*D12/2^*((S1^*T1 + S2^*T2)aOm)$$
$$dV/dac = -Ic^*D34/2^*((S3^*T3 + S4^*T4)/aOc)$$

where Im and Ic are the intensities of the measurement beam and the control beam, respectively. D12 and D34 are the gains of the differential means; Sj (j = 1 ... 4) are the photovoltaic conversion factors, and Tj (j = 1 ... 4) are the transductance factors. By varying D12 and D34 or Tj it is possible to make dV/dam = −dV/dac, in which case the same deviation in the measurement beam and in the control beam produces signals of the same module but of opposite signs, and then V(am, ac) remains unchanged. The heating of the sample causes the deflection of the measurement beam but not that of the control beam, and the various noise sources (except for the electronic source) affect both beams. If the bias has the same intensity, frequency and phase, the value of V(am(t), ac(t)) does not vary. This is essentially the case of the instability in the sighting of the analyzing laser beam and of the mechanical vibrations, if the measurement beam and the control beam hit the centre of the respective couples of photodiodes and if the optical doubling and focusing means of the sample have been mounted integral with one another.

From the foregoing it is evident that the device according to the invention is adapted to avoid the effects on the measurement due to the noise, in particular those relative to the instability of the direction of the laser beam and to the mechanical vibration, with respect to the effects due to other noise sources. As already mentioned in the introduction, this object is achieved without using a laser having high sighting of the beam and an expensive, cumbersome, optical anti-vibration bench.

The present invention has been illustrated and described according to a preferred embodiment but it should be understood that structural modifications can be made without parting from the scope of the present invention.

We claim:

1. An optoelectronic device for measuring the optical absorption in thin layer material using the photothermal deflection spectroscopy, comprising an optical splitter means which receives a light beam from a laser and divides the light beam into two parallel light beams, one for use as a measurement beam and the other as a control beam, to rectify the effects due to the mechanical vibrations of the device, said optical splitter means allowing the shifting of said two light beams parallely and in the same direction, in response to mechanical vibrations of said device, in such a way that they constantly keep at a preset mutual distance, the measurement beam being transported into a sample area lighted by a pump beam, while the control beam follows the same optical path producing a signal which is due only to the mechanical vibration of the system, the shifting of each beam being measured by one sensor comprised of two position sensors mounted integrally with one another.

2. The device of claim 1, wherein said optical splitter means comprise a beam splitter separating the input beam into two beams of similar intensity having directions orthogonal to each other, and a prism having a total internal reflexion, said prism being placed downstream of said splitter.

3. The device of claim 2, wherein the mutual positions and orientations of the measurement beam and the control beam are provided by positioning said total internal reflexion prism.

4. The device of claim 3, including a cylindrical converging lens which focuses both said measurement beam and said control beam in the area adjacent to the sample to be measured.

5. The device of claim 3, wherein the sensor is divided into four sectors forming two couples evenly illuminated by the measurement beam and the control beam.

6. The device of claim 3, including a cylindrical converging lens and wherein the optical doubler and cylindrical converging lens of the input beam are assembled to be integral with one another.

7. The device of claim 2 wherein the sensor is divided into four sectors forming two couples evenly illuminated by the measurement beam and the control beam under non-absorption conditions.

8. The device of claim 7, wherein said four sectors of the sensor generate four photocurrents conveyed to an electronic circuit the output of which is a linear combination thereof with alternate signs so as to eliminate from the measurement the effects due to instability of the laser beam and mechanical vibrations.

9. The device of claim 2, including a cylindrical converging lens which focuses both said measurement beam and said control beam in the area adjacent to the sample to be measured.

10. The device of claim 2, including a cylindrical converging lens and wherein the optical doubler and cylindrical converging lens of the input beam are assembled to be integral with one another.

11. The device of claim 2, including a cylindrical converging lens placed between the optical splitter means and the sample.

12. The device of claim 1 including a cylindrical converging lens placed between the optical splitter means and the sample.

13. The device of claim 12, wherein said cylindrical converging lens focuses both a measurement beam and a control beam in the area adjacent to the sample to be measured.

14. The device of claim 13, wherein the sensor is divided into four sectors forming two couples evenly illuminated by the measurement beam and the control beam.

15. The device of claim 13, wherein the optical doubler and cylindrical converging lens are assembled to be integral with one another.

16. The device of claim 12, wherein the optical splitter and focusing means of the analyzing beam are assembled to be integral with one another.

* * * * *